(12) United States Patent
Yotsutsuji (10) Patent No.: US 11,071,830 B2
(45) Date of Patent: Jul. 27, 2021

(54) HIGH-SLIDABILITY SYRINGE

(71) Applicant: COKI ENGINEERING INC., Osaka (JP)

(72) Inventor: Akira Yotsutsuji, Osaka (JP)

(73) Assignee: COKI ENGINEERING INC., Osaka (JP)

( * ) Notice: Subject to any disclaimer, the term of this patent is extended or adjusted under 35 U.S.C. 154(b) by 454 days.

(21) Appl. No.: 16/071,435

(22) PCT Filed: Mar. 29, 2016

(86) PCT No.: PCT/JP2016/001822
§ 371 (c)(1),
(2) Date: Jul. 19, 2018

(87) PCT Pub. No.: WO2017/168461
PCT Pub. Date: Oct. 5, 2017

(65) Prior Publication Data
US 2020/0338272 A1    Oct. 29, 2020

(51) Int. Cl.
*A61M 5/315* (2006.01)
*A61M 5/31* (2006.01)

(52) U.S. Cl.
CPC ...... *A61M 5/31513* (2013.01); *A61M 5/3129* (2013.01); *A61M 5/31515* (2013.01); *A61M 2005/3131* (2013.01); *A61M 2205/0216* (2013.01); *A61M 2205/0222* (2013.01)

(58) Field of Classification Search
CPC ............ A61M 5/31513; A61M 5/3129; A61M 5/31515; A61M 2005/3131; A61M 2205/0216; A61M 2205/0222; A61M 2005/31521; A61M 5/28
See application file for complete search history.

(56) References Cited

U.S. PATENT DOCUMENTS

2010/0204658 A1    8/2010   Imai

FOREIGN PATENT DOCUMENTS

| CN | 101348610 A | 1/2009 |
| CN | 102231994 A | 11/2011 |
| CN | 202875977 U | 4/2013 |

(Continued)

OTHER PUBLICATIONS

International Search Report dated Jun. 14, 2016 for international Application No. PCT/JP2016/001822.

(Continued)

*Primary Examiner* — Theodore J Stigell
*Assistant Examiner* — Rachel T. Smith
(74) *Attorney, Agent, or Firm* — Lucas & Mercanti, LLP (57) ABSTRACT

A high-slidability syringe has high safety and sealability over a long period of time. The syringe includes a gasket having a lower sliding resistance to a syringe barrel. The syringe includes: a syringe barrel; a gasket adapted to be press-fitted in the syringe barrel and used in a sliding manner in the syringe barrel; and a piston rod with the gasket attached to a front end thereof. The gasket includes: a gasket main body that is formed of a rigid plastic having resistance to a drug solution to be loaded into the syringe barrel and has a recessed groove formed in a sliding contact surface thereof adapted to slidably contact an inner circumferential surface of the syringe barrel; and a sliding contact ring that is fitted in the recessed groove.

7 Claims, 5 Drawing Sheets

(56) References Cited

FOREIGN PATENT DOCUMENTS

| CN | 103547273 | A |   | 1/2014 |              |
|----|-----------|---|---|--------|--------------|
| CN | 103930144 | A |   | 7/2014 |              |
| GB | 1031950   | A |   | 6/1966 |              |
| JP | 05131029  | A | * | 5/1993 |              |
| JP | H05-131029| A |   | 5/1993 |              |
| JP | 2000-342688| A |  | 12/2000 |             |
| JP | 2000342688| A | * | 12/2000 | ........ A61M 5/31513 |
| JP | 2006181027| A | * | 7/2006 | ........ A61M 5/31513 |
| JP | 2009-505794| A |  | 2/2009 |             |
| WO | 2009/001600| A1|  | 12/2008 |             |
| WO | 2013/033453| A2|  | 3/2013 |             |
| WO | 2014/136138| A1|  | 9/2014 |             |

OTHER PUBLICATIONS

CNIPA, Office Action for the corresponding Chinese patent application No. 201680081185.0, dated May 21, 2020 (English translation not available).

Extended European Search Report dated Mar. 25, 2019 from the corresponding European Patent Application No. 16896683.6.

CNIPA, Office Action for the corresponding Chinese patent application No. 201680081185.0, dated Nov. 25, 2020 (a concise explanation of the relevance is included in the attached transmittal letter).

IP India, Office Action for the corresponding Indian Patent Application No. 201827029351, dated Jan. 29, 2021.

CNIPA, Office Action for the corresponding Chinese Patent Application No. 201680081185.0, dated Apr. 20, 2021 with an machine English translation.

* cited by examiner

HIGH-SLIDABILITY SYRINGE

This application is a 371 of PCT/JP2016/001822 filed Mar. 29, 2016, and his application is incorporated by reference herein.

TECHNICAL FIELD

The present invention relates to a high-slidability syringe that allows a piston rod (plunger) to be pushed for injection with much less pressing force both on its initial movement and during the subsequent forward movement, without being affected by silicone oil.

BACKGROUND ART

An injection syringe without an injection needle includes a syringe barrel (cylindrical tube) made of plastic or glass, a movable piston rod, a gasket attached to a front end portion of the piston rod, and a top cap attached to a needle mount part of the syringe barrel.

For the gasket, a vulcanized rubber (butyl rubber) is conventionally used in order to prevent leakage of an injection solution.

However, it has been considered that all elastomers including butyl rubbers have no slidability with respect to contacting objects.

Thus, in order to improve the poor slidability of the above-mentioned conventional rubber gasket with respect to the inner circumferential surface of the syringe barrel, silicone grease is conventionally applied to the surface of the gasket and the inner circumferential surface of the syringe barrel.

Application of silicone grease dramatically reduces the sliding resistance.

The present inventor actually prepared gasket main bodies each having a recessed groove by using the materials shown in Table 1, fitted various types of rubber rings into the recessed grooves, and then conducted sliding tests to be described later so as to measure the sliding resistances of these rubbers.

The rubber rings thus prepared each had a length of 2 mm and a diameter larger by 0.2 mm than the inner diameter of the syringe barrel. The gasket main body was kept from contact with the inner circumferential surface of the syringe barrel so as to detect the sliding resistance of each rubber ring only.

As a result, butyl rubber did not slide and other rubbers exhibited a sliding resistance of 20 N or more, as shown in Table 1.

When a doctor or a nurse manually pushes a piston rod of an injection syringe for an injection, this sliding resistance is too high for him/her to push the piston rod smoothly.

In this case, the required sliding resistance is up to 8 N, and it is believed that the lower sliding resistance is more preferable.

Even when an injection device in which an injection syringe is mounted is used to push a piston rod of the injection syringe mechanically, the piston rod does not move smoothly if the sliding resistance is 20 N or more.

Even mechanical pushing using the injection device requires a sliding resistance of 15 N or less.

TABLE 1

| Elastomer type | Sliding resistance without application of silicone grease | Sliding resistance with application of silicone grease |
| --- | --- | --- |
| Butyl rubber | Not slidable | 5 to 8N |
| Nitrile rubber | 20N or more | 5 to 8N |
| Urethane rubber | 20N or more | 5 to 8N |
| Fluorine rubber | 20N or more | 5 to 8N |
| Silicone rubber | 20N or more | 5 to 8N |
| Ethylene propylene rubber | 20N or more | 5 to 8N |
| Polyisoprene rubber | 20N or more | 5 to 8N |
| Polybutadiene rubber | 20N or more | 5 to 8N |
| Chloroprene rubber | 20N or more | 5 to 8N |

Table 1 is a table showing the sliding resistances of various types of elastomers, which were compared by the inventor. Silicone grease has a dramatic effect of improving the sliding resistance of the rubber gasket to the inner circumferential surface of the syringe barrel, and the resulting sliding resistance is 5 to 8 N (see Table 1).

However, when the silicone grease is applied to the surface of the rubber gasket or the inner circumferential surface of the syringe barrel as described above, the silicone grease comes in direct contact with a drug solution in the syringe barrel. As a result the silicone grease reacts with an active ingredient in the drug solution and the drug solution deteriorates (for example, the active ingredient particles aggregate around fine particles of the silicone oil as the nuclei), or the drug solution is contaminated with silicon fine particles separated from the silicone grease and the contaminated solution adversely affects human health. These issues have been identified as problems.

There is also a risk that soluble components in the rubber may dissolve into the drug solution.

In particular, pre-filled syringes, which have been widely used in recent years, are previously filled with a drug solution, stored for a long period of time, and used in various environments. Therefore, gaskets for such pre-filled syringes are required to have higher capabilities than those for ordinary injection syringes.

Examples of the required capabilities include: (a) being safe to use without deteriorating the drug solution even if the gasket is in contact with the drug solution for a long period of time; (b) ensuring tight sealing against a highly permeable drug solution (liquid tightness that prevents leakage of the drug solution from between the gasket and the syringe and water vapor impermeability that prevents outward permeation of water contained in the drug solution through the gasket); and (c) having slidability comparable to that of an ordinary injection syringe (a sliding resistance of 8 N or less is preferable and the lower sliding resistance is more preferable when the piston rod of the injection syringe is manually pushed, or a sliding resistance of 15 N or less is preferable when the piston rod is mechanically pushed using an injection device).

Another problem is identified. If a gasket is held still in a pre-filled syringe stored for a long period of time, the gasket adheres to a portion of the inner wall of the syringe barrel and is firmly fixed to that portion, resulting in tendency to increase the pressure required for the initial movement when an injection is given, which makes it hard to use such a syringe.

Thus, in order to solve these problems, Patent Literature 1 proposes, as a measure to improve slidability, a combination of a thermoplastic or thermosetting elastomer having a Shore A hardness of 30 to 80 (butyl rubber typically has a Shore A hardness of 40 to 50) and a rigid plastic material (hereinafter simply referred to as a rigid plastic) such as a medical grade polypropylene having high chemical resistance.

More specifically, the proposed gasket is obtained by preparing rigid plastic cores (corresponding to gasket main bodies) of various shapes having an outer diameter smaller than the inner diameter of a syringe barrel and fitting, onto each of the cores, a ring-shaped elastic sleeve made of an elastomer having "rubber elasticity" to prevent leakage of liquid.

Patent Literature 2 discloses, as another example, a gasket that is entirely made of a slidable silicone rubber obtained by mixing silicone oil and polyethylene powder into silicone rubber and vulcanizing the resulting mixture.

CITATION LIST

Patent Literature

[PTL 1] Japanese Laid-Open Patent Publication (Translation of PCT Application) No. 2009-505794 (paragraph 0012)

[PTL 2] Japanese Laid-Open Patent Publication No. 05-131029 (paragraphs 0008 to 0015)

SUMMARY OF INVENTION

Technical Problem

However, most of conventionally known elastomers having the above-described "rubber elasticity" also have very high "sliding resistance" to contacting objects.

In other words, since an elastomer that exhibits high "slidability" without using silicone grease that dramatically improves slidability has not been known up to now, application of silicone grease to the inner circumferential surface of a syringe has been considered essential to obtain slidability required for practical use.

Therefore, a contact between an injection solution and silicone grease cannot be avoided in fact in the injection syringe described in Patent Literature 1.

On the other hand, a gasket that is entirely made of a slidable silicone rubber is disclosed as in Patent Literature 2, but in this gasket, the added silicone oil, even if the amount thereof is very small, cannot be prevented from exuding to the surface of the gasket and coming into contact with the loaded injection solution to contaminate it.

Even if the slidable silicone rubber of Patent Literature 2 is applied to the elastic sleeve of Patent Literature 1, a liquid contact side flange (corresponding to a liquid contact side sliding part) of the core of Patent Literature 1 is narrower than the outer diameter of the elastic sleeve (corresponding to a sliding contact ring) and forms a gap from the inner circumferential surface of the syringe barrel. Thus, even if the elastic sleeve is press-fitted in the syringe barrel, the gap still exists between the inner circumferential surface of the syringe barrel and the liquid contact side flange of the core. Therefore, there is a risk that the loaded drug solution may flow into the gap and come into contact with the elastic sleeve and then with the silicone oil that has bled (exuded) to the surface of the elastic sleeve, resulting in contamination of the loaded drug solution.

Thus, in order to solve the above-described problems, the inventor uses a medical grade rigid plastic such as PTFE (polytetrafluoroethylene) for a "gasket main body" adapted to be in direct contact with the injection solution, modifies the structure of the gasket main body to form a structure in which a "sliding contact ring" is kept from contact with the injection solution, and uses, for this "sliding contact ring", a "slidable silicone rubber" that allows silicone grease to bleed under increased pressure or increased temperature.

A first object of the present invention is to obtain an innovative high-slidability syringe that has high safety and sealability over a long period of time and includes a gasket having a lower sliding resistance to a syringe barrel, for example, a sliding resistance of 7 N or less during manual pushing of a piston rod of an injection syringe (with a volume of 1 to 5 ml), including at least the initial movement of the piston rod.

Solution to Problem

A high-slidability syringe A according to claim 1 includes: a syringe barrel 1; a gasket 10 adapted to be press-fitted in the syringe barrel 1 and used in a sliding manner in the syringe barrel 1; and a piston rod 5 with the gasket 10 attached to a front end thereof. In this high-slidability syringe A, the gasket 10 includes: a gasket main body 26 that is formed of a rigid plastic having resistance to a drug solution 30 to be loaded into the syringe barrel 1 and has a recessed groove 18 formed in a sliding contact surface 11 thereof adapted to slidably contact an inner circumferential surface 2 of the syringe barrel 1; and a sliding contact ring 19 that is fitted in the recessed groove 18. The sliding contact ring 19 includes: a rubber base material (elastomer) 19$c$ that, when silicone oil is added thereto, allows the silicone oil to bleed therefrom under increased pressure on the sliding contact ring 19 against the syringe barrel 1; and the silicone oil added to the rubber base material 19$c$, and has an outer diameter D1 larger than an inner diameter D0 of the syringe barrel 1. The gasket main body 26 includes: a liquid contact side sliding contact surface 11$a$ that is provided between a liquid contact side end surface 14 and the recessed groove 18 and has an outer diameter D2 larger than the inner diameter D of the syringe barrel 1; and a rod side sliding contact surface 11$b$ that is provided between a rod side end surface 17$a$ and the recessed groove 18 and has an outer diameter D3 equal to or smaller than the inner diameter D0 of the syringe barrel 1.

Since the rubber base material 19$c$ of the sliding contact ring 19 is a material that, when silicone oil is added thereto, allows the silicone oil to bleed therefrom under increased pressure on the sliding contact ring 19 against the syringe barrel 1, the silicone oil bleeds to the surface of the sliding contact ring 19 over time (for example, at least 24 hours). The bleeding is promoted by increasing the temperature (see FIG. 4). It should be noted that in FIG. 4, as described later, silicone oil is added but ultrahigh molecular weight polyethylene powder is not added to silicone rubbers.

Figure 3:
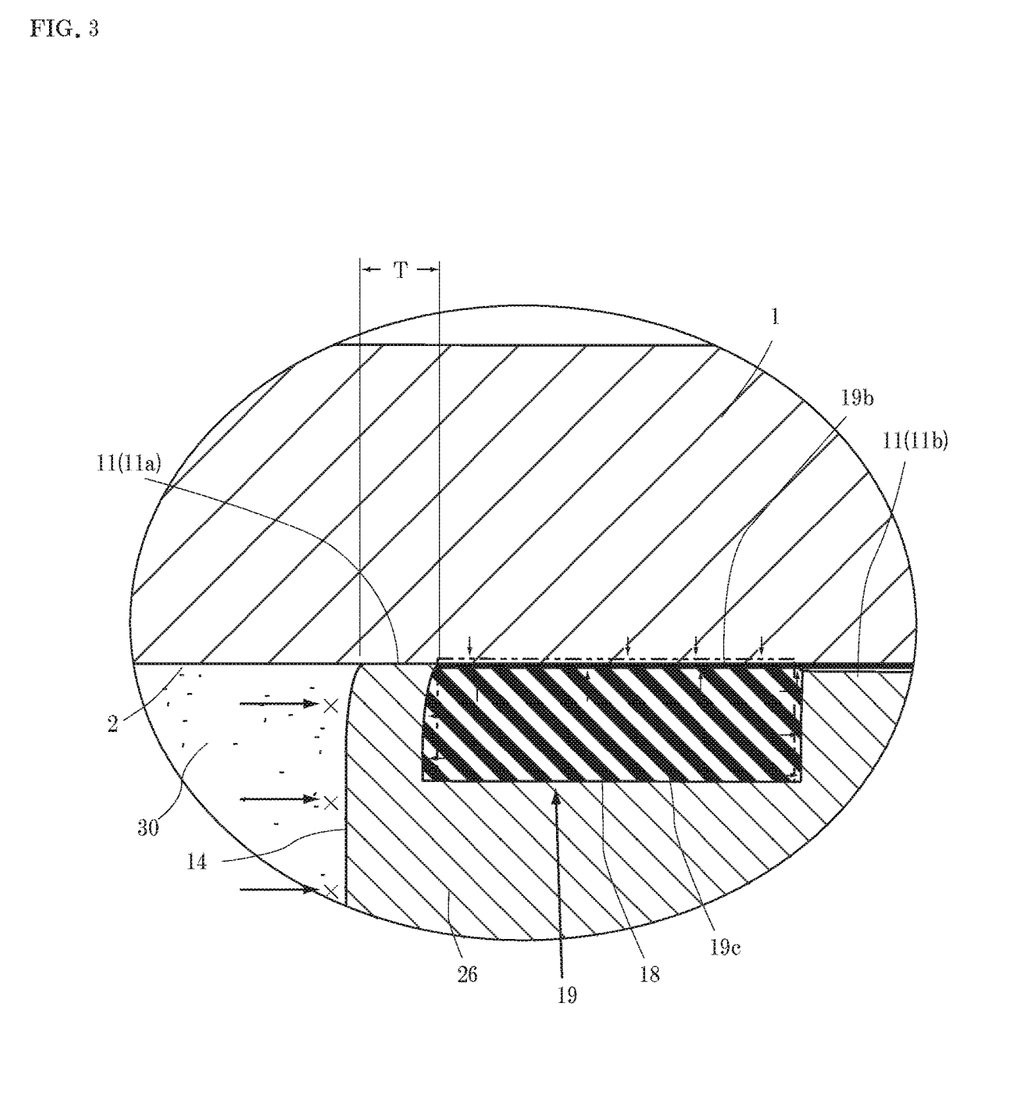
FIG. 3 is an enlarged partial front view of a portion indicated by an ellipse drawn by a broken line in FIG. 1.

When this gasket 10 is attached to the piston rod 5 and press-fitted in the syringe barrel 1, the internal pressure of the sliding contact ring 19 is increased as it is compressed by the inner circumferential surface 2 of the syringe barrel 1, and as a result, the silicone oil bleeds. When the pre-filled syringe A filled with the drug solution 30 is left at high temperature (for example, 25° C. to 30° C.), the bleeding is promoted. FIG. 3 shows a silicone oil film 19$b$ formed of the bleeding silicone oil.

The presence of the thin bleeding silicone oil film 19$b$ between the sliding contact ring 19 and the inner circumferential surface 2 of the syringe barrel 1 improves the slidability of the sliding contact ring 19 with respect to the inner circumferential surface 2 of the syringe barrel 1 more significantly than the absence of the bleeding silicone oil film 19b.

On the other hand, since the outer diameter D2 of the liquid contact side sliding contact surface 11a of the gasket main body 26 located on the liquid contact side of the sliding contact ring 19 is larger than the inner diameter D0 of the syringe barrel 1, the liquid contact side sliding contact surface 11a is pushed strongly by the inner circumferential surface 2 of the syringe barrel 1 and maintains the sealing thereof. Thus, the bleeding silicone oil is blocked by the liquid contact side sliding contact surface 11a and prevented from exposure to the drug solution 30.

In contrast, since the outer diameter D3 of the rod side sliding contact surface 11b is equal to or smaller than the inner diameter D0 of the syringe barrel 1, when a large amount of silicone oil bleeds, the bleeding silicone oil escapes to the side of the piston rod 5 through a small gap between the rod side sliding contact surface 11b and the inner circumferential surface 2 of the syringe barrel 1. Thus, exposure of the silicone oil to the drug solution 30 is prevented with certainty.

Claim 2 is directed to the high-slidability syringe A according to claim 1, wherein the rubber base material (elastomer) 19 of the sliding contact ring 19 is a silicone rubber.

Claim 3 is directed to the high-slidability syringe A according to claim 1 or 2, wherein the sliding contact ring 19 is fitted in contact with a liquid contact side sliding part 16 provided between the liquid contact side end surface 14 and the recessed groove 18 of the gasket main body 26.

Thereby, the liquid contact side sliding part 16 is supported by the sliding contact ring 19 during the forward movement of the gasket 10 for an injection, and thus the thickness of the liquid contact side sliding part 16 can be reduced to the utmost limit to reduce the sliding resistance of the liquid contact side sliding part 16 to the inner circumferential surface 2 of the syringe barrel 1.

Claim 4 is directed to the high-slidability syringe A according to any one of claims 1 to 3, wherein an ultrahigh molecular weight polyethylene fine powder is further added to the rubber base material (elastomer) 19c.

Figure 5:
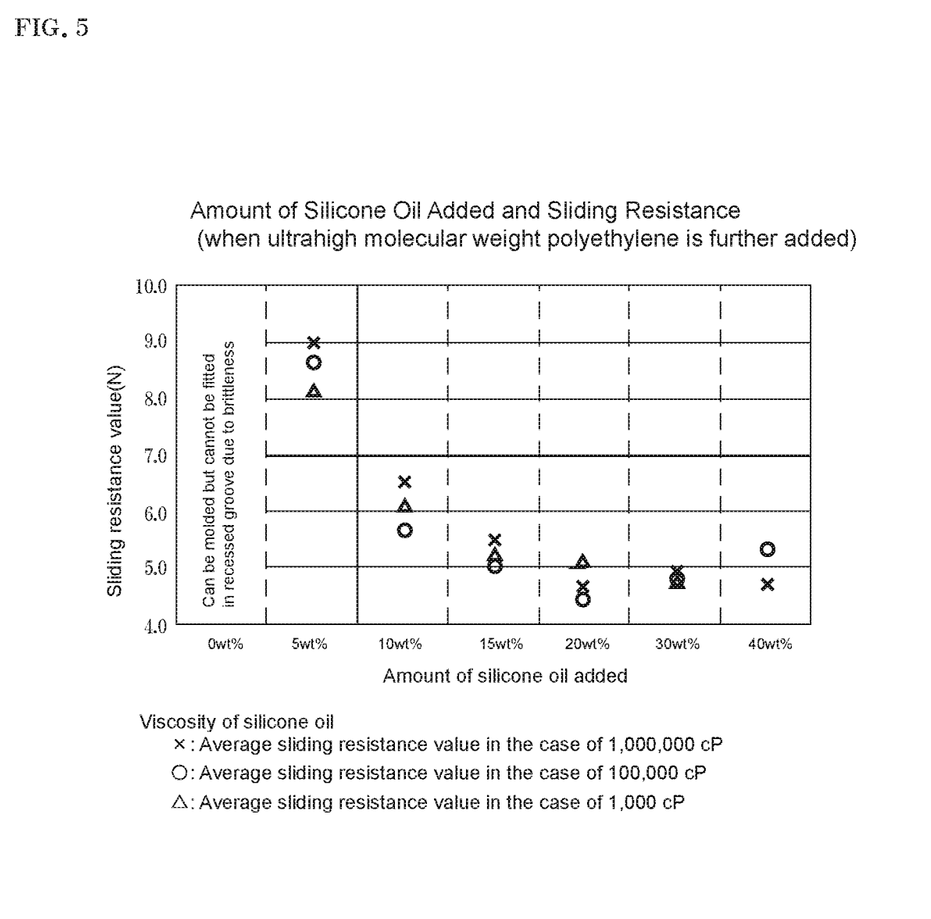
FIG. 5 is a graph showing changes with the amount of added silicone oil in sliding resistance of gaskets of the present invention, each of which is equipped with a sliding contact ring obtained by adding both silicone oil and ultrahigh molecular weight polyethylene powder.

By adjusting the content of the ultrahigh molecular weight polyethylene fine powder, it is possible not only to optimize the hardness of the rubber base material (elastomer) 19c for the sliding contact ring 19 but also to increase the content of the silicone oil more significantly than in the absence of the ultrahigh molecular weight polyethylene fine powder (FIG. 5).

Figure 1:
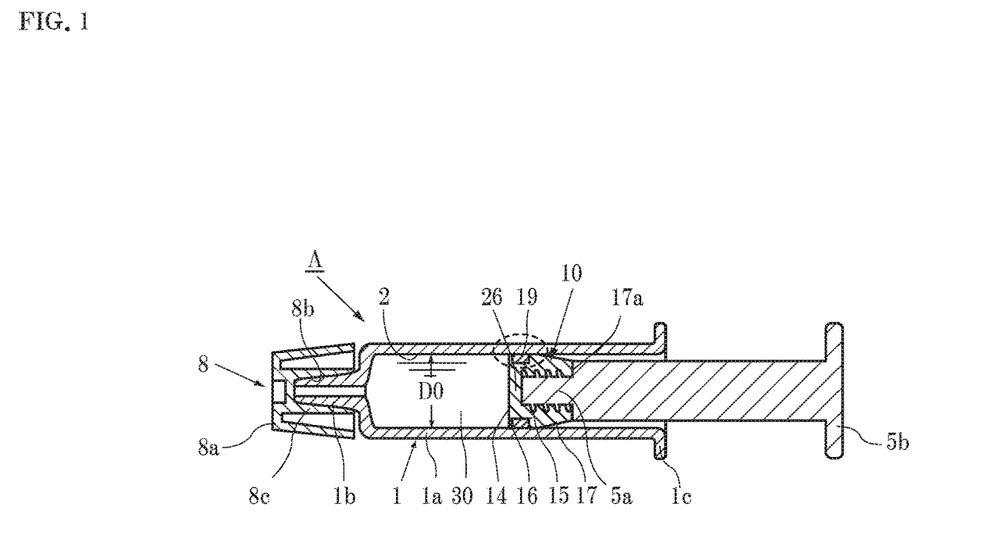
FIG. 1 is a cross-sectional view of a pre-filled syringe of the present invention.

Claim 5 is directed to the high-slidability syringe A according to any one of claims 1 to 4, wherein the rigid plastic that forms the entire main body portion 26 of the gasket 10 (also referred to as the gasket main body 26) shown in FIG. 1 is any one of the following hard materials that are non-reactive with the drug solution 30 (drug solution-resistant rigid plastics): fluorine resins having a Shore D hardness of 40 or more, such as PTFE (polytetrafluoroethylene), PFA (tetrafluoroethylene-perfluoroalkyl vinyl ether copolymer), FEP (copolymer of tetrafluoroethylene and hexafluoropropylene), PCTFE (polychlorotrifluoroethylene), and PVDF (polyvinylidene fluoride); PP (polypropylene); ultrahigh molecular weight polyethylene; COP (cycloolefin polymer); and COC (ethylene-norbornene copolymer).

These materials are all highly resistant to chemicals and suitably used as materials for the gasket main body 26.

Claim 6 is directed to the high-slidability syringe A according to any one of claims 1 to 5, wherein the liquid contact side sliding contact surface 11a has a sliding contact width T of 0.1 mm or more and 0.6 mm or less.

When the gasket main body 26 having the liquid contact side sliding contact surface 11a with a sliding contact width T within the above-mentioned range is press-fitted in the syringe barrel 1, the liquid contact side sliding part 16 is flexibly deformed and comes into contact with the inner circumferential surface 2 of the syringe barrel 1 so as to maintain the sealing thereof. When the sliding contact width T is less than 0.1 mm, the liquid contact side sliding part 16 does not have sufficient strength and loses its sealability. When the sliding contact width T is more than 0.6 mm, the liquid contact side sliding part 16 has too much strength, loses its flexibility, and thus loses its sealability and slidability as well.

When the gasket 10 has dimensions within the above-mentioned range, it can be used not only in a plastic syringe barrel 1 having higher dimensional accuracy but also in a glass syringe barrel 1. In the case of a glass syringe barrel 1, it is preferable that the sliding contact ring 19 has a supporting function due to a small thickness of the liquid contact side sliding part 16.

Claim 7 is directed to the high-slidability syringe A according to claim 6, wherein the syringe barrel 1 is formed of glass or plastic (such as COP, PP, or COC).

Advantageous Effects of the Invention

In the gasket 10 according to the present invention, a rigid plastic, such as PTFE, that is non-reactive with the drug solution 30, is used for the gasket main body 26, and the sliding contact ring 19 that allows the contained silicone oil to bleed is used in a portion of the gasket main body 26 configured not to come into contact with the drug solution 30. Thereby, the high-slidability syringe A can exhibit a slidability high enough to meet the requirement not only for the sliding movement of the gasket but also for the initial movement thereof.

DESCRIPTION OF EMBODIMENTS

Hereinafter, the present invention will be described in accordance with illustrated embodiments. FIG. 1 is a cross-sectional view of the pre-filled syringe A of the present invention that has just been unpacked. Although not shown here, in an ordinary disposable syringe in a package, a gasket 10 mounted on a piston rod 5 is press-fitted in a syringe barrel 1 with no pre-filled drug solution 30, and a top cap 8 is attached to the front end of the syringe.

The pre-filled syringe A will be described below as a representative example.

As shown in FIG. 1, after being unpacked, the pre-filled syringe A includes the gasket 10, the syringe barrel 1 filled with the drug solution 30, the piston rod 5 with the gasket 10 attached thereto, and the top cap 8.

The syringe barrel 1 is a cylindrical container including: a barrel main body 1a; a mount part 1b that is provided in a protruding manner at the front end of the barrel main body 1a and to which an injection needle not shown is to be attached; and a flange 1c for finger placement that is formed at the back end. For the material of the syringe barrel 1, glass, hard resin (e.g., cycloolefin resin (hereinafter referred to as "COP"), polypropylene (hereinafter referred to as "PP"), ethylene-norbornene copolymer (hereinafter referred to as "COC"), etc. are used. When the seal width T (to be described later) of the gasket main body 26 is 0.1 to 0.6 mm (preferably 0.1 to 0.3 mm), the gasket main body 26 fits well with the inner circumferential surface 2 of the syringe barrel. Therefore, not only a resin syringe barrel 1 but also a glass syringe barrel 1 can be used, although the dimensional accuracy of the inner diameter of the glass syringe barrel 1 is lower than that of the resin syringe barrel 1.

The piston rod 5 is a rod-shaped member having a male screw part 5a provided at the front end part and a finger rest part 5b provided at the back end. On the outer circumferential surface of the male screw part 5a of this piston rod 5, a male screw thread to be screwed into a female screw hole 15 of the above-mentioned gasket main body 26 is formed. The material of the piston rod 5 is, for example, a resin such as cyclic polyolefin, polycarbonate, or polypropylene.

The top cap 8 is a sealing member that is attached to the needle mount part 1b of the syringe barrel 1 to prevent leakage of the drug solution 30 filled in the syringe barrel 1 and to prevent contamination of the drug solution 30 with airborne germs, etc. This top cap 8 includes a cap main body 5a having a truncated cone shape, and an engagement protrusion 8c extending from the top surface of this cap main body 8a toward the opening and having a recess 8b in which the needle mount part 1b is to be fitted. The top cap 8 is formed of an elastomer having a drug solution-resistant film layer (PTFE or PFA) formed on the inner circumferential surface thereof. Examples of the elastomer include "vulcanized rubbers", "thermosetting elastomers", and "thermoplastic elastomers".

The main body portion 26 of the gasket 10 shown in FIG. 1 is entirely formed of one of hard materials that are non-reactive with the drug solution 30 (drug solution-resistant rigid plastics) such as: fluorine resins such as PTFE (polytetrafluoroethylene), PFA (tetrafluoroethylene-perfluoroalkyl vinyl ether copolymer), FEP (copolymer of tetrafluoroethylene and hexafluoropropylene), PCTFE (polychlorotrifluoroethylene), and PVDF (polyvinylidene fluoride); PP (polypropylene); ultrahigh molecular weight polyethylene; COP (cycloolefin polymer); and COC (ethylen-norbornene copolymer).

A rigid plastic having a Shore A hardness of at least 70 (or a Shore D hardness of 40 to 100 or a Rockwell M hardness of 40 to 70) is suitably used in the present invention.

The PTFE used in the present invention may be pure PTFE, but it is more preferable to use a PTFE modified with 1 to 15 mass % of fluorine resin, such as a polytetrafluoroethylene-perfluoralkyl vinyl ether copolymer (abbreviated as "PFA") or a tetrafluoroethylene-hexafluoropropylene copolymer as a crystallization inhibitor for PTFE, so as to impart elasticity to the main body portion 26 of the gasket 10.

As the PTFE for use in the present invention, not only the above-mentioned pure PTFE and modified PTFE but also a closed cell foam block (round bar material) obtained by so-called hot isostatic pressing (HIP) can be used.

A primary sintered FE block is obtained by compression molding and sintering pure PTFE powder or modified PTFE powder. In the resulting sintered body, powder particles are in close contact with each other, but very fine voids are formed between non-contact portions as a whole and these voids are connected to allow a small amount of fluid to pass through.

When this primary sintered PTFE block is hot isotropic pressed, the block is compressed and the ultrafine voids formed between PTFE particles are certainly closed to form a closed cell structure. Hot isostatic pressing under reduced pressure is more effective.

Next, the shape of the gasket 10 in FIG. 1 will be described. The main body portion 26 of the gasket 10 has a columnar shape, and the back end surface thereof is provided with a female screw hole 15 in which the piston rod 5 is fitted. The outer circumferential surface of the front end side of the main body portion 26 is a sliding contact surface 11 adapted to slidably contact the inner circumferential surface 2 of the syringe barrel 1, and a portion 17 extending from the sliding contact surface 11 to a piston rod mounting surface 17a serving as the back end surface is tapered such that the diameter of the portion 17 gradually decreases. This portion is referred to as a tapered portion 17. The material of the main body portion 26 is as described above.

A shallow recessed groove 18 is formed over the entire circumference of the middle portion of the above-mentioned sliding contact surface 11 of the main body portion 26.

In other words, narrow sliding contact surfaces 11a and 11b are formed on both sides of the recessed groove 18, and the liquid contact side sliding contact surface 11a adjacent to the liquid contact surface 14 with respect to the drug solution 30 is imparted with liquid tightness.

Specifically, the liquid contact side sliding contact surface 11a is formed to have an outer diameter D2 that is slightly larger than the inner diameter D0 of the syringe barrel 1, and thus a portion having this liquid contact side sliding contact surface 11a (i.e., a liquid contact side sliding part 16) is press-fitted in the syringe barrel 1 with a predetermined press-fit margin.

For the gasket 10 having dimensions within the above-mentioned range, not only a plastic syringe barrel 1 but also a glass syringe barrel 1 can be used.

On the other hand, the rod side sliding contact surface 11b is formed to have an outer diameter D3 that is equal to or slightly smaller than the inner diameter D0 of the syringe barrel 1, and thus slides with a very low sliding resistance to serve as a guide for the sliding gasket 10.

A sliding contact ring 19 adapted to slidably contact the inner circumferential surface 2 of the syringe barrel 1 is fitted in the recessed groove 18. In a cross section taken along the axis of the main body portion 26, the shape of the bottom of the recessed groove 18 is straight, convex toward the opening of the recessed groove 18, or concave in the opposite direction. The outer circumference of the sliding contact ring 19 fitted in the recessed groove 18 has a shape that conforms to the shape of the bottom of the recessed groove 18.

Any material can be used for the rubber base material to form the sliding contact ring 19 as long as, when silicone oil is added to the material, the material allows the silicone oil contained therein to bleed at least under increased pressure.

"The bleeding of the added silicone oil" refers to the phenomenon in which (a) the added silicone oil exudes to the surface of the rubber base material 19c after being allowed to stand at least under increased pressure for 24 hours, and (b) the bleeding is promoted at increased temperature.

Since the present invention is directed to a syringe, the rubber base material 19c that forms the sliding contact ring 19 is preferably a material already approved for medical use. An example of such a material is "silicone rubber" imparted with slidability.

"Silicone rubber" as the rubber base material is a thermosetting resin, and liquid or pasty "organopolysiloxane" as the raw material is a material having a methyl group, a vinyl group, a phenyl group, or a trifluoropropyl group in the molecule thereof depending on the special properties required. There are two types of "silicone rubber". Any type of silicone rubber can be used in the present invention. An example thereof is a peroxide-crosslinking silicone rubber obtained by adding a filler required and a peroxide curing agent to a liquid or pasty "organopolysiloxane" having a vinyl group therein, kneading the mixture, and then causing the mixture to undergo a curing reaction to form a rubber with a desired molecular weight.

Another example is an addition-reaction type silicone rubber obtained by heat curing a clayey polysiloxane having a vinyl group in the molecule thereof and a clayey polysiloxane having a reactive hydrogen at the molecular terminal thereof, through a reaction using platinum, rhodium, or an organic tin compound as a catalyst.

The above-mentioned silicone rubber having slidability is formed, for example, by adding a peroxide as a crosslinking agent to a liquid or pasty organosiloxane as a base material (or adding a curing catalyst to the above-mentioned two types of clayey polysiloxanes), further adding a predetermined amount of silicone oil, and kneading the mixture in a kneader.

An appropriate amount (for example, 25%) of fine silica powder is further added to adjust the hardness of the kneaded product. In addition, for example, a predetermined amount of ultrahigh molecular weight polyethylene fine powder is added, if necessary.

The polyethylene resin that forms fine particles in the above-mentioned fine powder has an ultrahigh molecular weight (for example, an average molecular weight of 1,000,000 to 3,000,000 or even higher up to 7,000,000 in some cases).

Such ultrahigh molecular weight particles have no water permeability and stick to almost nothing.

Since ultrahigh molecular weight polyethylene has such a high molecular weight, it does not melt even at a high temperature and maintains its spherical form even when it is molded under a high pressure.

The surface of the spherical ultrahigh molecular weight polyethylene is relatively smooth, but some irregularities are also observed.

The particle size of the spherical ultrahigh molecular weight fine particles contained in the fine powder ranges from 10 to 300 μm. More preferably, the particle size is 20 to 50 μm. Particles having an average particle size of 25 μm, 30 μm, or another size are used, although the particle size depends on the grade of the particles.

When the powder has a wide particle size distribution, small size particles fit into the voids between large size particles to fill them, and thus close packing is achieved.

When close-packed, fine particles have no water permeability. Therefore, even if a silicone rubber base material having water permeability or silicone oil is used, the slidable silicone rubber for medical use of the present invention exhibits very low water permeability as a whole.

Silica fine powder is a powder made from silica sand as a raw material and consists mainly of silicon ($SiO_2$). Silica fine powder is added to the rubber base material to adjust the hardness.

Silicone oil is, in general, a clear, colorless liquid having high heat resistance, cold resistance, and water resistance, and its viscosity shows little change over a wide range of temperatures. In addition, silicone oil has releasing, water repellent, defoaming, and lubricating properties. Silicone oil having a higher viscosity is preferably used in the present invention, and the viscosity as a measure of the molecular weight is preferably in a range of 1,000 to 1,000,000 cP, and more preferably in a range of about 50,000 to 200,000 cP, to allow the silicone oil to bleed.

The kneaded silicone oil and the rubber base material 19c are compatible with each other. Therefore, when an appropriate amount of silicone oil is added to the rubber base material 19c, the silicone oil spreads uniformly within the rubber base material 19c, bleeds over time (in at least 24 hours) at least under increased pressure, and exudes to the surface of the rubber base material 19c to form a thin layer thereon.

The method for molding the sliding contact ring 19 is as follows. A compression mold capable of molding the sliding contact ring 19 is heated to, for example, 150° C. to 160° C., filled with the above-mentioned molding material (i.e., the silicone rubber obtained by adding silica powder, silicone oil, and ultrahigh molecular weight PE powder, if necessary, and kneading the mixture), and heated and pressurized for 1 to 10 minutes to cause thermal crosslinking to occur. Thus, the desired sliding contact ring 19 is obtained.

The outer diameter D1 of the sliding contact ring 19 is slightly larger than the outer diameter D2 of the liquid contact side sliding contact surface 11a of the liquid contact side sliding part 16 of the main body portion 26, so that the sliding contact ring 19 comes into close contact with the inner circumferential surface 2 of the syringe barrel 1 to ensure liquid tightness.

It should be noted that the width of the sliding contact ring 19 is set to be slightly smaller than the width of the recessed groove 18 into which the sliding contact ring 19 is to be fitted so as to form gaps S between them, so that when the gasket 10 is press-fitted in the syringe barrel 1, the compressed sliding contact ring 19 is pushed out in the longitudinal direction of the gasket main body 26 and comes into contact with the back surface of the liquid contact side sliding contact surface 11a so as to support the liquid contact side sliding contact surface 11a from behind.

Next, the method for producing the main body portion 26 will be described. The main body portion 26 is produced using a drug solution-resistant rigid plastic that is resistant to the drug solution 30 to be loaded in the syringe barrel 1, as described above. The use of PTFE will be described below as an example.

Lathe cutting or injection molding can be used to form the above-mentioned shapes, but only cutting can be used for PTFE.

Figure 2:
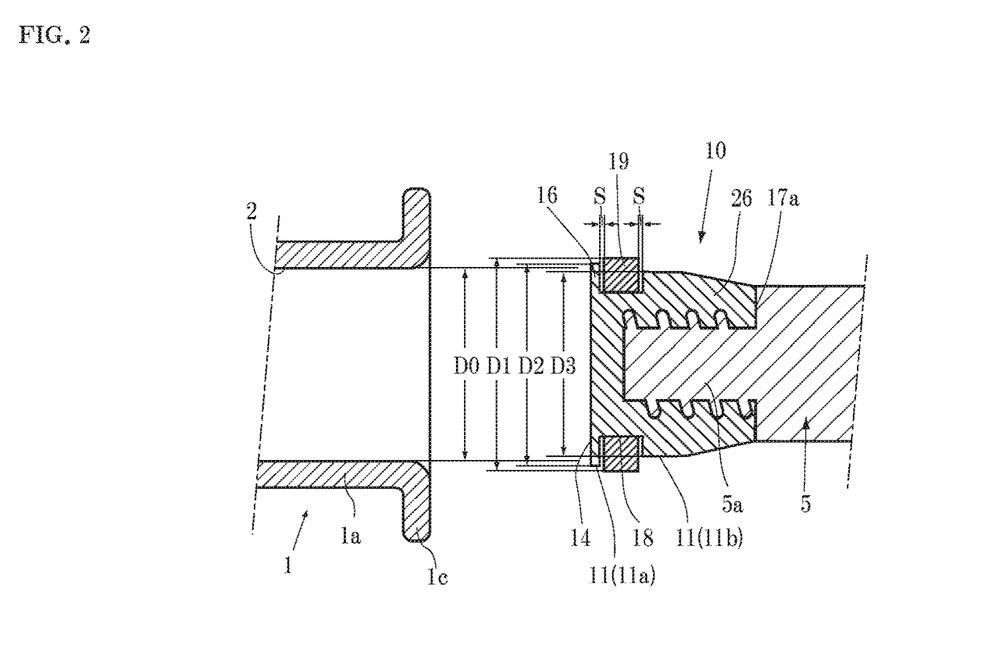
FIG. 2 is an enlarged partial cross-sectional view showing a gasket adapted to be press-fitted into the syringe.

PTFE (polytetrafluoroethylene) used as a material to be processed is cut to obtain the gasket main body 26 shown in FIG. 2.

The PTFE material is cut so that the liquid contact side sliding contact surface 11a of the liquid contact side sliding part 16 of the gasket main body 26 that plays an important role for water tightness have a width (referred to as a sliding contact width T) of 0.1 to 0.6 mm (more preferably 0.1 to 0.3 mm). (Needless to say, injection molding can also be used for materials other than PTFE to form the same shape).

Then, the above-mentioned sliding contact ring 19 is fitted into the recessed groove 18 of the gasket main body 26 to form the gasket 10. Before the gasket 10 is press-fitted into the syringe barrel 1, the width of the recessed groove 18 in which the sliding contact ring 19 is fitted is larger than the width of the sliding contact ring 19 to form small gaps S on both sides of the sliding contact ring 19 (FIG. 2).

When the components as described above are assembled, the sliding contact ring 19 is compressed by the syringe barrel 1 to fill the above-mentioned small gaps S, and thus comes into contact with the thin liquid contact side sliding part 16 and supports this part 16 from behind. Thereby, even with the liquid contact side sliding part 16 having such a small thickness of about 0.1 mm, prevention of leakage of the injection solution 30 is ensured when an injection is given.

Then, the dug solution 30 is loaded into the space enclosed by the syringe barrel 1 and the gasket 10. Thus, the pre-filled syringe A as shown in FIG. 1 is configured.

When the gasket 10 is press-fitted in the syringe barrel 1, the internal pressure is increased by the compression from the syringe barrel 1, silicone oil bleeds over time to form a thin silicone oil film 19b on the surface of the sliding contact ring 19 but does not leak to the liquid contact side.

The total sliding resistance of the pre-filled syringe A of the present invention is the sum of the sliding resistance of the sliding contact ring 19 and the sliding resistance of the gasket main body 26.

The sliding resistance of the sliding contact ring 19 is about 4 to 5 N due to the presence of the bleeding silicone oil film 19b. The sliding resistance of this part can be reduced to about 4 to 6 N by adjusting the sliding contact width T of the liquid contact side sliding contact surface 11a of the gasket main body 26 and the press-fit margin of the liquid contact side sliding part 16 with respect to the syringe barrel 1 (i.e., half the difference in diameter therebetween).

This pre-filled syringe A can be made ready for use by simply removing the top cap 8 and attaching a predetermined needle to the needle mount part 1b.

During the use of the syringe A, the movement of the piston rod 5, including the initial movement thereof, is very smooth when it is moved either manually or mechanically.

Likewise, the gasket 10 including the sliding contact ring 19 maintains its high slidability over a long period of time not only at ordinary temperatures due to its high water repellency and water impermeability but also even after refrigerated storage due to the creep resistance of the sliding contact ring 19.

In addition, neither leakage of liquid nor permeation of water vapor occurs in the gasket 10 and at the sliding contact surface 11a with respect to the inner circumferential surface 2.

It should be noted that the pre-filled syringe A achieved the above-described capabilities even after an accelerated test (6-month storage in environments at 5° C. and 40° C.) performed taking into account various environments in which the syringe A might be used.

It is thus possible to provide an inexpensive pre-filled syringe A having satisfactorily high slidability, water vapor impermeability, and water tightness such as resistance to water leakage not only at ordinary temperatures but also even after refrigerated storage (or when used in a high-temperature environment), regardless of size from a small diameter to a large diameter, without the need to apply a gasket covering film for medical use to the gasket or to apply silicone oil to the inner circumferential surface of the syringe barrel.

Unlike the pre-filled syringe A described above, a syringe without the drug solution 30 is a disposable syringe as mentioned above. The disposable syringe also includes the gasket 10 press-fitted in the syringe barrel 1. Therefore, when the gasket is used, silicone oil bleeds to the surface of the sliding contact ring 19 under compression, and thus the piston rod 5 moves very smoothly with a sliding resistance of about 4 to 6 N.

It should be noted that the pre-filled syringe A, in particular, may be left at high temperature before use. In this case, the bleeding is promoted while the syringe is left, and the piston rod 5 moves more smoothly.

EXAMPLES

Figure 4:
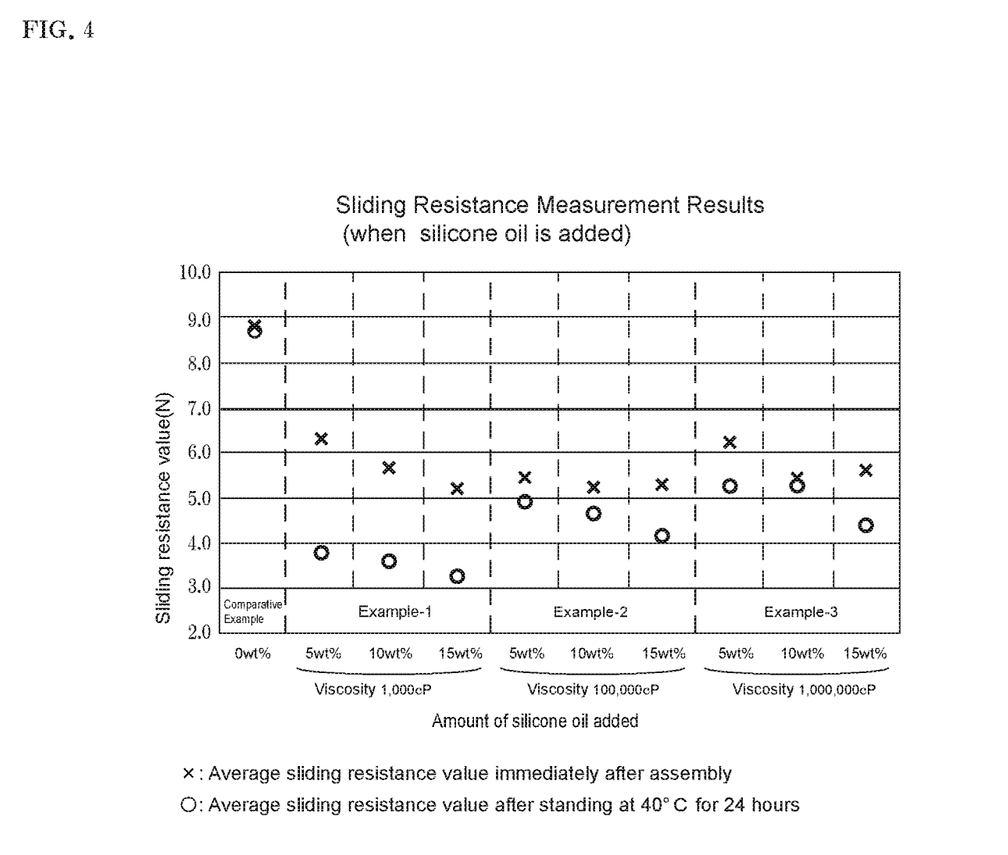
FIG. 4 is a graph showing changes with temperature in sliding resistance of gaskets of the present invention, each of which is equipped with a sliding contact ring obtained by adding silicone oil.

Evaluation of Slidability by Addition of Silicone Oil (FIG. 4)

The slidability of the high-slidability syringe was evaluated by the following experiments.

(Unit: mm)

Dimensions of Syringe (with a volume of 1 ml)
  Inner diameter: 6.35
  Sliding distance of gasket: 35
Dimensions of Gasket (Main Body Portion)
  Outer diameter of liquid contact side sliding part: 6.47
  Dimensions of recessed groove: groove width 1.6, diameter 5.2
  Seal width of liquid contact side sliding surface: 0.3
  Material: polytetrafluoroethylene
Dimensions of Sliding Contact Ring
  Thickness: 1.55
  Outer diameter 6.20
  Inner diameter: 4.5
  Material: 25 wt % of silica powder was added to polydimethylsiloxane and the mixture was kneaded to obtain a base material 1 (not containing silicone oil) (Comparative Example). On the other hand, 5 wt %, 10 wt %, and 15 wt % of silicone oil having a viscosity of 1,000 cP, 5 wt %, 10 wt %, and 15 wt/o of silicone oil having a viscosity of 100,000 cP, and 5 wt %, 10 wt %, and 15 wt % of silicone oil having a viscosity of 1,000,000 cP, respectively, were added to the base material 1 to obtain materials (Examples 1 to 3). Then, the average sliding resistances of these materials were measured immediately after each gasket was press-fitted in the syringe barrel and after the press-fitted gasket was allowed to stand at 40° C. for 24 hours to determine changes in the average sliding resistance (in Comparative Example and Examples 1 to 3, ultrahigh molecular weight polyethylene powder was not added).

The measurement results were as follows. Syringes each including a gasket equipped with a sliding contact ring prepared by adding 5 to 15 wt % of silicone oil showed an average sliding resistance of 7 N (unit: newton) or less immediately after the assembly. After standing at 40° C. for 24 hours, bleeding of silicone oil was promoted and the resulting average sliding resistance was lower than the above value.

In FIG. 4, since ultrahigh molecular weight polyethylene powder is not added, the content of silicone oil is limited up to 15 wt %. If the amount of silicone oil added is more than 15 wt %, it is difficult to mold the resulting mixture. If the amount of silicone oil added is less than 5 wt %, the resulting sliding resistance is higher than 7 N as the target value. The content of silicone oil that allows the syringe to be used immediately after the assembly is 5 to 15 wt %, and the content of silicone oil that allows the syringe to be used after the bleeding is promoted is 2.5 to 15 wt %, and more preferably 5 to 15 wt %.

Evaluation of Slidability by Addition of Ultrahigh Molecular Weight Polyethylene Fine Powder (FIG. 5)

In the evaluation of (FIG. 5), the gasket main body and the sliding contact ring having the same dimensions as those in FIG. 4 were used. In this evaluation, a base material (hereinafter referred to as a base material 2) was prepared by mixing 13.13 g of polydimethylsiloxane, 4.37 g of silica powder as a filler, and 23.35 g of ultrahigh molecular weight polyethylene powder (20 to 200 μm), and polydimethylsiloxane oils having various degrees of polymerization (polydimethylsiloxane oil is hereinafter referred to as silicone oil, and the viscosity of the silicone oil is represented in terms of cP as a measure of the degree of polymerization), that is, silicone oils having various viscosities of 1,000 to 1,000,000 cP, were added to the base material 2. Then, the relationship between the amount of silicone oil added and the sliding resistance was measured.

Ultrahigh molecular weight polyethylene powder has high compatibility with silicone oil. Therefore, not only the amount of silicone oil added could be increased, but also the hardness of the sliding contact ring could be increased by adding ultrahigh molecular weight polyethylene powder. The increased amount, i.e., 5 to 40 wt %, of silicone oil could be added.

In the case where 5 to 40 wt % of silicone oil having various viscosities were added, the resulting sliding resistances were less than 7 N as the target value. If the amount of added silicone oil is less than 5 wt %, the sliding resistance exceeds 7N as the target value. It should be noted that when more than 40 wt % of silicone oil was added, it was difficult to mold the resulting mixture.

It should be noted that if more than 40 wt % of silicone oil having a viscosity of 1,000 cP is added, it is impossible to mold the resulting mixture.

In this case, the optimum amount of silicone oil to be added is about 20 wt %.

Figure 6:
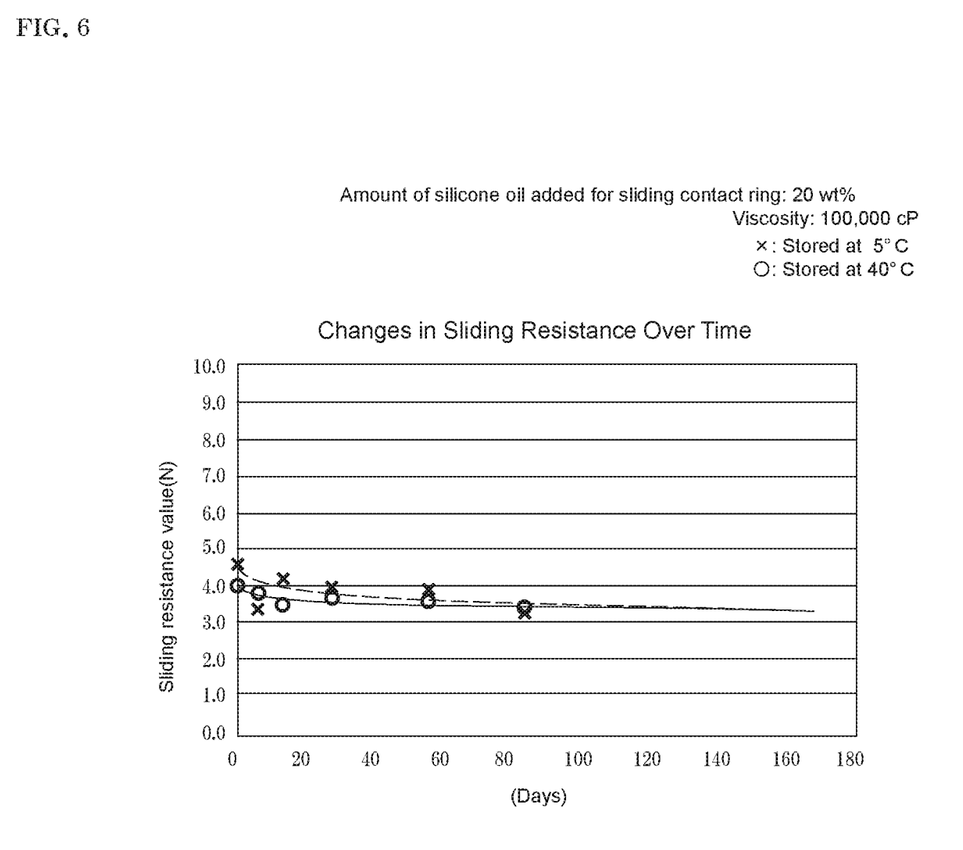
FIG. 6 is a graph showing changes over time in sliding resistance according to the present invention.

Changes in Sliding Resistance Over Time (FIG. 6)

FIG. 6 shows the changes in the sliding resistance over time in the case of 20 wt % addition shown in FIG. 5.

Sliding was performed at 100 mm/min as a measurement condition.

The silicone oil bled as time passed and the slidability was improved. This experiment revealed that bleeding was promoted in the case of storage at 40° C. and the sliding resistance was further reduced. After about 80 day-storage, a comparable sliding resistance was observed in both cases.

REFERENCE SIGNS LIST

A: High-slidability syringe
D0: Inner diameter of syringe barrel
D1: Outer diameter of sliding contact ring
D2: Outer diameter of liquid contact side sliding part
D3: Outer diameter of rod side sliding part
S: Gap
T: Sliding contact (seal) width of liquid contact side sliding part
1: Syringe barrel
1a: Barrel main body
1b: Needle mount part
1e: Flange
2: Inner circumferential surface
5: Piston rod
5a: Male screw part
5b: Finger rest part
8: Top cap
8a: Cap main body
8b: Recess
8c: Engagement protrusion
10: Gasket
11: Sliding contact surface
11a: Liquid contact side sliding contact surface
11b: Rod side sliding contact surface
14: Liquid contact side end surface
15: Female screw hole
16: Liquid contact side sliding part
17: Tapered portion
17a: Piston rod mounting surface (Rod side end surface)
18: Recessed groove
19: Sliding contact ring
19b: Bleeding silicone oil film
19c: Rubber base material (elastomer)
26: Main body portion (gasket main body)
30: Drug solution

The invention claimed is:

1. A high-slidability syringe comprising:
a syringe barrel;
a gasket adapted to be press-fitted in the syringe barrel and used in a sliding manner in the syringe barrel; and
a piston rod with the gasket attached to a front end thereof, wherein
the gasket comprises: a gasket main body that is formed of a rigid plastic having resistance to a drug solution to be loaded into the syringe barrel and has a recessed groove formed in a sliding contact surface thereof adapted to slidably contact an inner circumferential surface of the syringe barrel; and a sliding contact ring that is fitted in the recessed groove,
the sliding contact ring comprises: a rubber base material that, when silicone oil is added thereto, allows the silicone oil to bleed therefrom under increased pressure on the sliding contact ring against the syringe barrel; and the silicone oil added to the rubber base material, and has an outer diameter larger than an inner diameter of the syringe barrel, and
the gasket main body comprises: a liquid contact side sliding part adjacent to a liquid contact side end surface; and a rod side sliding part adjacent to a rod side end surface, the liquid contact side sliding part having a liquid contact side sliding contact surface that is provided between the liquid contact side end surface and the recessed groove and has an outer diameter larger than the inner diameter of the syringe barrel, and the rod side sliding part having a rod side sliding contact surface that is provided between the rod side end surface and the recessed groove and has an outer diameter equal to or smaller than the inner diameter of the syringe barrel.

2. The high-slidability syringe according to claim 1, wherein the rubber base material of the sliding contact ring is a silicone rubber.

3. The high-slidability syringe according to claim 1, wherein the sliding contact ring is fitted in contact with the liquid contact side sliding part provided between the liquid contact side end surface and the recessed groove of the gasket main body.

4. The high-slidability syringe according to claim 1, wherein an ultrahigh molecular weight polyethylene fine powder is further added to the rubber base material.

5. The high-slidability syringe according to claim 1, wherein the rigid plastic that forms the gasket main body is a fluorine resin having a Shore D hardness of 40 or more, or any one of polypropylene, ultrahigh molecular weight polyethylene, cycloolefin polymer, and ethylene-norbornene copolymer.

6. The high-slidability syringe according to claim 1, wherein the liquid contact side sliding contact surface has a sliding contact width of 0.1 mm or more and 0.6 mm or less.

7. The high-slidability syringe according to claim 6, wherein the syringe barrel is formed of glass, or any one of cycloolefin polymer, ethylene-norbornene copolymer, and polypropylene.

* * * * *